M. Mattson,
Syringe.
No. 1,797. Reissued Oct. 18, 1864.
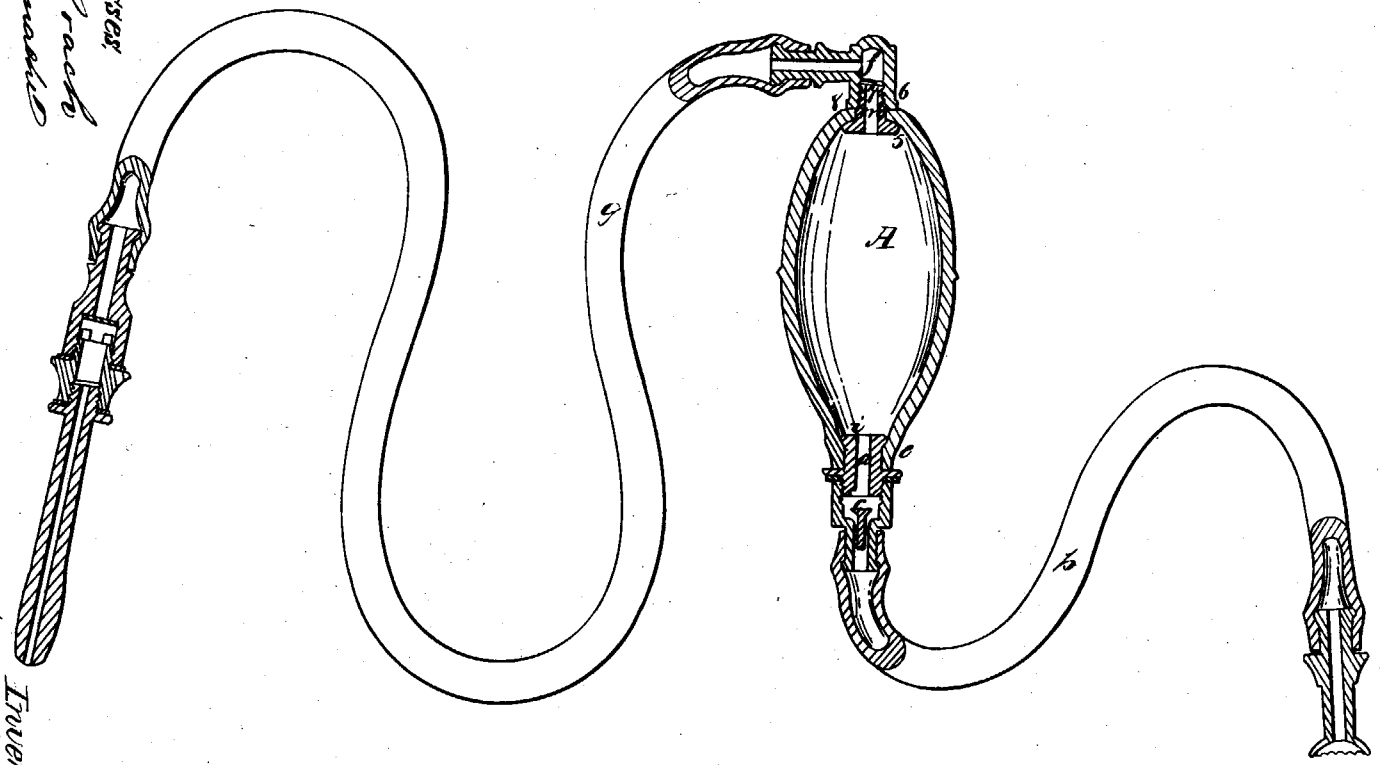
Witnesses:
Thos. R. Roach
F. E. Teschemacher
Inventor.
Morris Mattson
AM. PHOTO-LITHO. CO. N.Y. (OSBORNE'S PROCESS.)

UNITED STATES PATENT OFFICE.

MORRIS MATTSON, OF NEW YORK, N. Y.

IMPROVEMENT IN ENEMA SYRINGES.

Specification forming part of Letters Patent No. 33,747, dated November 19, 1861; Reissue No. 1,797, dated October 18, 1864.

*To all whom it may concern:*

Be it known that I, MORRIS MATTSON, late of Boston, in the county of Suffolk and State of Massachusetts, now of the city, county, and State of New York, have invented certain Improvements in Enema Syringes, of which the following is a specification.

This invention relates to that class of syringes known as "elastic-bulb syringes," in which an elastic bulb of sufficient elastic power for that purpose is made by its elasticity to exhaust the air from the induction pipe or tube so as to allow the fluid to flow through said pipe or tube into the bulb, and by the bulb being compressed the said fluid is forced through the eduction pipe or tube to its destination. Much difficulty has been found in securing a permanently tight joint at the point where the bulb unites with the metallic fastenings which connect it to the induction and eduction tubes. In the ordinary mode of construction the bulb is made with a small tubular neck which is slipped over an enlargement in the metallic fastening upon a neck formed thereon, and the contractile power of this elastic neck, which is slightly smaller before being stretched than the metallic fastening, is relied on to produce a tight joint, though in some instances I believe some sort of cement has been introduced between the parts, in the hope that it might add to the security of the joint. These joints, when new, are usually tight, but after being used they frequently become leaky, because the strain constantly thrown upon the neck of the bulb when in use by the alternate compression of the bulb by the hand and its expansion by its own elasticity has a tendency to work the neck of it loose upon the neck of the tube to which it is connected and to cause its permanent enlargement. Furthermore, the constant strain put upon the neck of the bulb by being placed around a rigid neck of larger diameter than its own natural internal caliber has a tendency to and does weaken its force of contraction and reduces its ability to press or draw itself tightly around the neck of the tube which connects the bulb to the other parts.

The principal object of my invention is to overcome this difficulty and to so connect the elastic bulb of an enema syringe to the hollow tube or pipe which unites it to the other parts of the syringe as to secure a permanently tight junction of the said elastic bulb and the said pipe.

Another important object of my invention is to so construct and combine these parts as, while at the same time securing the object above stated, to also allow the induction and eduction tubes to be separated from the elastic bulb and again attached with ease and facility and in such a manner that the disconnection of the parts of the pipes or tubes which connect the bulb to the induction and eduction pipes shall cause no derangement of the parts which would at all interfere with their ready re-connection by any person of ordinary intelligence.

The accompanying drawing represents a syringe of the usual size in which the eduction pipe or tube is connected to the bulb in a manner involving my invention, the induction-pipe being connected by the means previously in use for that purpose to enable me to more conveniently illustrate and explain the difference between the two constructions. The bulb and its connections to the elastic tube are represented in section as made by a plane passing through the center, and the metal parts at the extreme ends of these flexible pipes are represented in the same manner, the flexible tubes themselves being represented as cut away at the necessary points to give an unobstructed view.

In the drawings, A represents the elastic bulb which performs the office in the syringe of the piston and cylinder of a suction and force pump—namely, to exhaust the air from the induction pipe or tube so as to cause the fluid to flow into the bulb, and to afterward force the fluid by compression out through the eduction pipe or tube. To produce both these effects it must possess sufficient elastic power to expand by its own elasticity with sufficient force to so reduce the atmospheric pressure in it and in the induction-tube as to cause the fluid to flow up into it from the vessel in which said fluid is contained, and must also be impervious to both air and water. To secure these qualities, these bulbs are generally made of vulcanized india-rubber of about the thickness represented in the drawing. The usual method of connecting the induction and eduction pipes to the bulb is shown at the lower end of the bulb A, where the metal pipe *a*, which contains the induction-valve *c*, and to which the india-rubber tube *b* is connected, is secured to the bulb by the elasticity of the neck of the india-rubber bulb, the neck *e* of the bulb being forced over a button or knob, *i*, on the end of the metal pipe *a*.

At the upper end of the bulb my improved mode of connecting the parts is represented, where the pipe *f*, by which the india-rubber tube *g* is connected with the bulb A, is secured to the bulb in such a manner that the joint will be tight, and at the same time the construction is such as to allow the pipe *f* and the tube *g* to be readily removed from the bulb when required and replaced without difficulty by any person of ordinary comprehension. To accomplish this a plug, *m*, made of some rigid material, usually metal, and having a button head or flange, 5, on the inner end, a screw-thread, 6, on its outer end, and a hole, 7, extending longitudinally through it, is fitted into the end of the bulb, which is made in the form represented in the drawing, the hole in the end of the bulb being made as small as consistent with the insertion of the plug *m* without injuring the rubber. The pipe *f* has a screw cut in it which fits the screw 6, and when properly connected it presses upon the end of the bulb and clasps it tightly between said pipe and the plug *m*, thus forming a perfectly tight and durable joint, and securing the connection of the bulb with the pipe from derangement.

When the induction and eduction pipes are attached to opposite ends of the bulb, the latter should be formed without the neck *e*, both ends of it being formed alike, and the head of the plug *m* may be forced through a small hole made in the end of the bulb, leaving the screw-shank in position to receive the pipe *f*, as before stated.

The construction I have described has the further advantage that while it performs the duty of securing a tight and permanent joint between the india-rubber bulb A and the pipe or pipes to which the flexible tubes are attached, it at the same time furnishes a ready means of connecting the tubes to and detaching them from the bulb, requiring no other joint for that purpose.

I claim—

1. The combination of the elastic self-expanding and self-filling enema-syringe bulb A, and the connector, composed of two parts, *m* and *f*, or their equivalent, so constructed and combined with the bulb A as to confine the latter between those parts, and at the time furnish a free opening for the induction and eduction of the fluid, not confining myself to the specific form and construction of parts described so long as I accomplish the same result by means substantially the same—that is to say, the parts being so combined that the elastic bulb of an enema syringe shall be connected to the pipe which forms in whole or in part a connection with one or more of the induction and eduction pipes by the said elastic bulb being clamped or compressed upon or against said pipe or connection, and thus forming a tight and durable joint, as set forth.

2. So constructing the plug *m* and so combining it with the elastic bulb A of an enema syringe and the connecting-pipe *f* that when the latter is removed for any purpose the plug *m* shall be retained in its place by the elasticity of the bulb A secure from accidental displacement, substantially as set forth.

3. The combination of the elastic bulb A, the connector *m f*, or its equivalent, and one or more flexible tubes, *g*, either for induction or eduction, substantially as and for the purpose set forth.

MORRIS MATTSON.

Witnesses:
THOS. P. HOW,
JAMES T. GRAHAM.